United States Patent [19]

Iwatschenko

[11] Patent Number: 4,798,593
[45] Date of Patent: Jan. 17, 1989

[54] STIFFENING OF PROBES

[75] Inventor: Peter Iwatschenko, Neunkirchen, Fed. Rep. of Germany

[73] Assignee: Pfrummer-Viggo GmH+Co. KG, Erlangen, Fed. Rep. of Germany

[21] Appl. No.: 23,992

[22] Filed: Mar. 10, 1987

Related U.S. Application Data

[63] Continuation of Ser. No. 806,739, Dec. 9, 1985, abandoned.

[30] Foreign Application Priority Data

Dec. 8, 1984 [DE] Fed. Rep. of Germany ....... 3444935

[51] Int. Cl.⁴ .............................................. A61M 5/18
[52] U.S. Cl. .................................... 604/164; 604/265; 128/657
[58] Field of Search ............... 604/281, 265, 270, 164, 604/285, 275; 128/657

[56] References Cited

U.S. PATENT DOCUMENTS

| 4,257,421 | 3/1981 | Beal | 604/265 |
| 4,306,563 | 12/1981 | Iwatschenko | 604/265 |
| 4,534,363 | 8/1985 | Gold | 604/265 |

FOREIGN PATENT DOCUMENTS 2541919  3/1977  Fed. Rep. of Germany ...... 604/280

Primary Examiner—Dalton L. Truluck
Assistant Examiner—Denise Whelton
Attorney, Agent, or Firm—Jordan and Hamburg

[57] ABSTRACT

A guide for the stiffening of a probe made of a flexible material is disposed in the probe during insertion of the probe into a body cavity, the guide being removed again after the probe has been inserted into the body cavity, the guide being a wire element provided with a coating of a biocompatible material of which at least the surface is hydrophilic.

8 Claims, 1 Drawing Sheet

STIFFENING OF PROBES

This application is a continuation, of application Ser. No. 806,739, filed Dec. 9, 1985 now abandoned.

The invention relates to a guide for the stiffening of probes made of very flexible materials during their insertion into body cavities, whereby the guide is again removed after the probe is inserted.

Such very bendable and highly flexible probes are usually made of a material of high molecular weight, such as silicone rubber or polyurethane, latex or the like, which has the required biocompatibility and is bendable over a relatively small radius without thereby kinking. The concept "probe" is here taken in the its broadest sense of the word and includes also catheters and endoscopes.

Such probes have to fulfill two different, competing requirements. On the one hand, they have to be sufficiently stiff so that they can be satisfactorily inserted into a body cavity of a patient, i.e., in a way which is as considerate as possible for the patient. This is especially then of particular importance when the patient cannot support the insertion by swallowing movements, for example, when the insertion is only possible by overcoming bodily reflexes. On the other hand, in the inserted state, such a probe has to be soft and flexible, because in some cases it remains in the body of the patient for extended periods of time and must neither disturb nor hinder the freedom of movement of the patient. If such probes remain for several days in the stomach or duodenum or also in other body cavities, they must not harden due to agents causing loss of softness, because otherwise decubital necroses could occur. A probe also has to be sufficiently bendable even over a small radius, for example, of 20 mm, even by an angle exceeding 90 degrees, in order to adjust to the curvatures of the body cavities, in particular, when the access path goes through the nose-throat cavity.

For the purpose of rendering them stiff for insertion in body cavities, PVC probes, for instance, are cooled before insertion (Federal Republic of Germany Auslegeschrift 21 40 994). An alternative thereof is the stiffening of the probe by means of a wire which is again removed from the probe after the probe is inserted. The disadvantage thereby is that placing the wire into the probe requires sophisticated handling and constitutes a danger of piercing the thin walls of the probe with a wire having a small cross-section. A wire end which penetrates through the probe wall can cause the patient unpleasant injuries. It is especially important that initially there is a possibly high friction between the wire and the probe in order to extensively exclude relative movement between wire and probe during the insertion process. However, this is diametrically opposed to the requirement of keeping the friction coefficient between the probe and wire as low as possible, so that the wire can be removed as effortlessly as possible after the probe is put in place.

For example, in BSI 63 14/1983 there are prescribed maximum forces of 5N for removing such a stiffening wire from a probe. A solution of this problem is shown in U.S. Pat. No. 397,535. Another solution, in which the use of a wire is not necessary, is described in Federal Republic of Germany Patent No. 28 51 547. Nevertheless, there are cases in which the use of the latter disclosed probe is not permissible, just as in other specific cases, it is indispensable to use a probe with a stiffening guide.

The object of the invention is based on the scope of the latter mentioned case with an embodiment of a guide of the initially indicated kind having the object of improving the handling of a wire-stiffened probe such that the insertion can be performed less dangerously and more considerately, and on the other hand, that the guide can be removed again from the probe considerably easier than previously. The danger of injuring the patient is thereby reduced to a minimum and especially considerate treatment of the patient is assured. For the solution of this problem, the invention provides for a guide of the above designated kind, whereby the wire is provided with a coating of a biocompatible material of which at least the surface is hydrophilic. Such wire is relatively thin. In general, it has a diameter of $0.2 \propto 0.4$ mm, and the coating, which can be provided by a dipping process or can be sprayed on the wire, can be kept so thin that a sufficient soft running of the guide during its insertion into the probe is assured. The hydrophilia, at least of the surface of the coating if not of the entire coating material, is required in order to effectively reduce the comparably high friction between the guide according to the invention and the inside wall of the probe, in that immediately before removing the guide from the inserted probe a biocompatible liquid, such as various body fluids or water, is introduced. Because of the hydrophilic properties of the wire surface, the guide can now be removed without problems from the inserted probe just by using a comparatively quite low pulling force. Investigations have shown that with the use of a guide configured according to the invention, the guide, in a test according to BSI, can be removed at a force of 0.5N to a maximum of 1N. A considerable improvement is thereby achieved with respect to conventional wire-stiffened probes, thus for the benefit of the patient as well as the personnel carrying out the treatment, by decisively reducing the risks of treatment requiring insertions of such probes.

It is within the scope of the invention to use gelatin as a coating for the wire which constitutes the guide. Gelatin is a material whis is available inexpensively, which can be processed without problems, and which, furthermore, is of neutral taste, so that it can be used practically everywhere. It is within the scope of the inventive concept to add to the gelatin constituting the coating of the wire a portion of biocompatible alcohol as a softening agent. For example, sorbite can be used as well as a polyhydric alcohol, for instance, glycerine. Generally, an addition of 0.5–5% glycerine is sufficient. If necessary, a portion of formaldehyde or of another aldehyde can be added to the gelatin in order to reduce the solubility of the gelatin.

In a further embodiment of the guide according to the invention, at the outer end of the wire thereof, there can be fastened a connector provided with a coupling part for the fastening of the probe end and a coupling part for the introduction of a lubricant, as well as a passage connecting the two coupling parts to each other. A guide embodied in this way makes possible an especially effortless introduction of the liquid serving as a lubricant between the probe and the guide as well as, furthermore, applying the required pulling force for the removal of the guide.

Suitably, the connector is provided with a mounting for receiving a loop arranged at one of the ends of the wire guide. This mounting can easily be arranged on the connector, which considerably facilitates applying the pulling force required for the removal of the guide.

It has proven especially advantageous to make the configuration such that the connector consists of two parts which can be assembled approximately in an axial plane, at the junction plane of the parts there is provided a recess for receiving the wire loop and the passage connecting the two coupling parts. For inserting the wire loop, the two parts are separated and are closed again over the wire loop of the guide.

It is within the scope of the invention that one of the coupling parts of the connector is configured as a seat for the outlet flange of a hypodermic syringe. In this way, the lubricant can be especially reliably introduced into the inside of the probe.

Further advantages, characteristics and particulars of the invention result from the following description of a preferred embodiment of the invention, as well as from the drawings, as follows:

DESCRIPTION OF THE PREFERRED EMBODIMENTS

Figure 1:
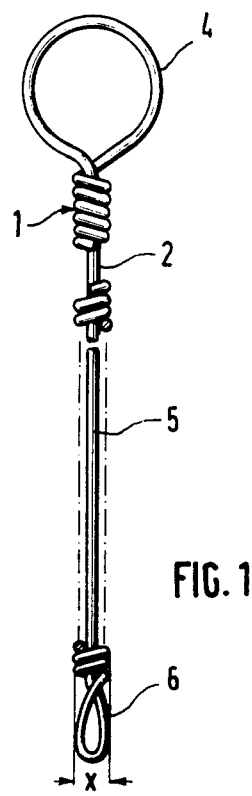
FIG. 1 is an elevated view of a guide according to one embodiment of the invention.
Figure 2:
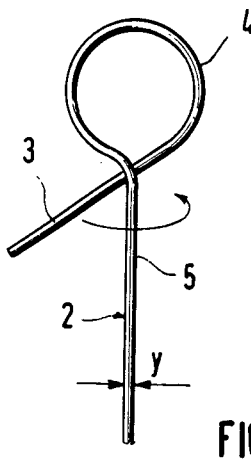
FIG. 2 is a detail view of the guide.
Figure 3:
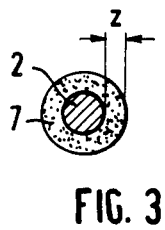
FIG. 3 is a section through the wire of the guide.
Figure 4:
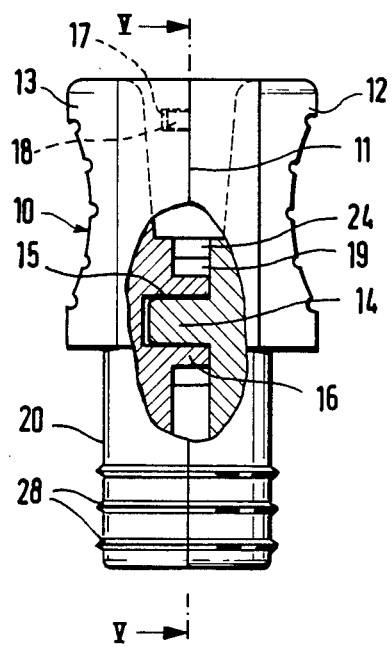
FIG. 4 is a view, partially broken away and in sections, of the connector.
Figure 5:
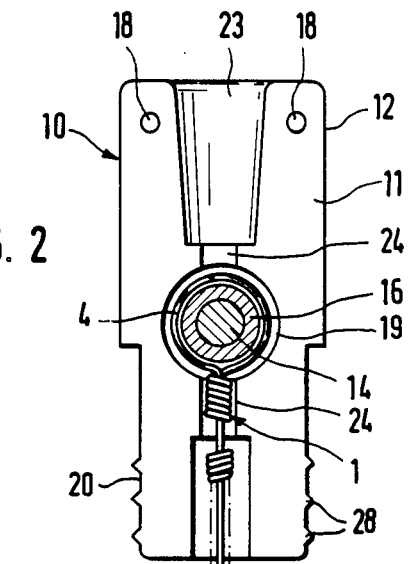
FIG. 5 is a sectional through the connector taken along the line V—V in FIG. 4.
Figure 5:
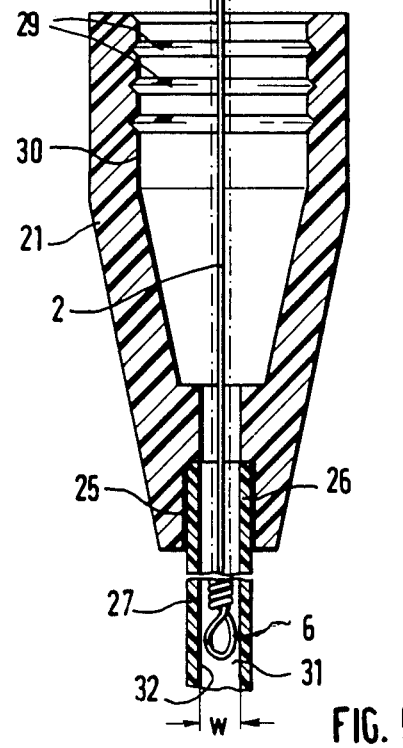

The guide 1 is formed from a wire 2 made of corrosion-resistant and biocompatible material such that one of the wire ends 3 is formed into a loop 4 and, as shown in FIG. 1, is coiled onto the elongated shaft 5 of the wire 2. The opposite end of the guide 1 is also formed into a loop 6, however, the maximum diameter thereof is considerably smaller than that of loop 4. The wire end is then coiled onto the elongated shaft 5 in the shape of a spiral so that practically the entire shaft 5 of the wire 2 has such coils. The diameter $X$ of the guide 1 corresponds approximately to that of the loop 6 at the inserting end. It can amount to approximately 0.9 mm.

The wire 2 serving for the embodiment of the guide 1 has a diameter y of approximately 0.05 mm, and is provided with a coating 7 made of a biocompatible material, for example gelatin, of a thickness z of 0.1–0.2 mm.

The wire loop 4 at the outer end of the guide 1 is fastened on a connector 10. The latter consists of two parts 12 and 13 which can be separated in an axial plane 11, whereby the part 12 is provided with a pin 14 for engaging the other part in the bore 15 of a sleeve 16. The thereby formed plug connection is completed by two further plug pins 18 which engage into respective bores 17 of the part 13. In the junction plane 11 of the two parts 12 and 13 there is provided a recess 19 corresponding to the profile of the loop 4 of the guide 1, with the recess 19 enclosing the coupling part 16 of the part 13.

On the connector 10 are provided two coupling parts, i.e., a plug 20 for the connection of an adapter piece 21 on the end 26 of the probe 6 and a channel 23, which serves as a seat for the not illustrated outlet flange of a hypodermic syringe or the like. Both coupling parts 20 and 23 are connected to each other by a passage 24 which also includes the recess 19 which receives the wire loop 4. The adapter piece 21 is provided with a channel 25 which tightly receives the end 26 of the probe 27. The adapter piece 21 conically widens approximately to the diameter of the plug 20 and can be fastened thereon in the seat, whereby ribs 28 at the outer circumference of the plug 20 come into contact with the groove-like indentations 29 on the inside 30 of the adapter piece 21.

By applying a syringe onto the channel 23 of the connector 10, a liquid lubricant can be introduced into the inner space 31 of the probe 27 which has a diameter w which is only slightly greater than the greatest outer diameter $X$ of the guide 1. This lubricant, which can be a body fluid or also water, with respect to the hydrophilic properties of the coating 7 of the guide 1, reduces the friction between the guide 1 and the inner wall 32 of the probe 27.

The basic concept of the invention, to provide the wire 2 serving for the shaping of the guide 1 with a hydrophilic coating, of course can also be envisioned with a guide having a different configuration than that shown, and it is also possible to contemplate a connector of a different configuration or to omit it entirely.

What is claimed is:

1. A guide for the stiffening of probes which are made of flexible material and in which the guide is disposed during insertion of the probe into a body cavity and is withdrawn from the probe after the probe has been inserted into the body cavity, comprising a single elongated wire guide element adapted to be inserted into and withdrawn from said probe, a coating on said wire guide element made of a biocompatible material of which at least the surface is hydrophilic, a connector fastened to an outer end of said wire guide element, said connector having a first coupling means for coupling said connector to said probe, and a second coupling means for coupling a lubricant-introducing device to said connector, said connector further having a passage providing communication between said first and second coupling means.

2. A guide according to claim 1, wherein said probe has an adapter element at an outer end thereof, said first coupling means coupling said adapter element to said connector.

3. A guide according to claim 2, wherein said first coupling means comprises a plug part, said adapter element having a channel receiving said plug part for effecting a coupling therebetween.

4. A guide according to claim 1, wherein the outer end of said wire guide element has a loop, said connector having a loopreceiving means for receiving said loop to thereby connect said wire guide element to said connector.

5. A guide according to claim 1, wherein said connector comprises two parts which are mated approximately along an axial junction plane, each of said two parts having a recess opening onto said junction plane, the outer end of said wire guide element having a loop which is received in said recess, said passage extending between said recess and said first and second coupling means.

6. A guide according to claim 1, wherein said second coupling means has a seating surface, said lubricant-introducing device being a syringe having an outlet flange which seats on said seating surface.

7. A guide according to claim 6, wherein said seating surface has a partial conical configuration.

8. A method of inserting a flexible probe element into a body cavity such as the stomach, duodenum or the like, comprising:

forming a single elongated stiff wire element having the necessary stiffness which would enable the stiff wire element to be inserted into said body cavity;

coating said stiff wire element with gelatin having biocompatible alcohol added thereto and providing a hydrophilic outer surface on said gelatin coating;

inserting said coated stiff wire element into a flexible probe element such that the stiff coated wire element imparts stiffening to said flexible probe element;

inserting said probe element with the coated stiff wire element therein into said body cavity;

reducing the friction between said stiff wire element and said flexible probe element by introducing a liquid into said flexible probe element such that such liquid contacts said hydrophilic surface to thereby effect the friction reduction between said gelatin coating and said flexible probe element;

utilizing said effect of friction reduction to facilitate withdrawal of said coated stiff wire element from said flexible probe element; and leaving said flexible probe element in said body cavity, whereby said stiff wire element provides the necessary stiffness to said flexible probe element to permit insertion of the latter into said body cavity while said gelatin coating reduces friction to facilitate withdrawal of said stiff wire element from said flexible probe element.

* * * * *